US009023862B2

(12) United States Patent
Pellicer-Martinez et al.

(10) Patent No.: US 9,023,862 B2
(45) Date of Patent: *May 5, 2015

(54) MEDICAMENT FOR THE TREATMENT OF ENDOMETRIOSIS

(71) Applicant: Ferring International Center S.A., St-Prex (CH)

(72) Inventors: Antonio Pellicer-Martinez, Valencia (ES); Carlos Simon-Valles, Godella-Valencia (ES); Edurne Novella-Maestre, Saragossa (ES)

(73) Assignee: Ferring International Center S.A., Saint-Prex (CH)

( * ) Notice: Subject to any disclaimer, the term of this patent is extended or adjusted under 35 U.S.C. 154(b) by 0 days.

This patent is subject to a terminal disclaimer.

(21) Appl. No.: 14/543,478

(22) Filed: Nov. 17, 2014

(65) Prior Publication Data

US 2015/0073010 A1   Mar. 12, 2015

Related U.S. Application Data

(63) Continuation of application No. 12/525,342, filed as application No. PCT/IB2008/001273 on Feb. 1, 2008, now Pat. No. 8,927,568.

(60) Provisional application No. 60/947,165, filed on Jun. 29, 2007.

(30) Foreign Application Priority Data

Feb. 1, 2007   (EP) .................................... 07250429
Jun. 29, 2007   (GB) .................................. 0712626.1

(51) Int. Cl.
*A61K 31/473*   (2006.01)
*A61K 9/34*   (2006.01)
*A61K 9/00*   (2006.01)

(52) U.S. Cl.
CPC ............. *A61K 31/473* (2013.01); *A61K 9/0034* (2013.01)

(58) Field of Classification Search
CPC .............................. A61K 31/473; A61K 9/34
USPC ....................................................... 514/290
See application file for complete search history.

(56) References Cited

U.S. PATENT DOCUMENTS

| 4,692,452 A | 9/1987 | Cerny et al. |
| 6,359,130 B1 | 3/2002 | Singh et al. |
| 8,334,298 B2 | 12/2012 | Pellicer-Martinez et al. |
| 2012/0157489 A1 | 6/2012 | Pellicer-Martinez et al. |

FOREIGN PATENT DOCUMENTS

| RU | 2273481 | 4/2006 |
| WO | 9303752 | 3/1993 |
| WO | 9640139 | 12/1996 |
| WO | 2006117608 | 11/2006 |

OTHER PUBLICATIONS

The abstract of Motta et al., Fertil Steril, 1996;65(2):440-2.*

(Continued)

*Primary Examiner* — San-Ming Hui
(74) *Attorney, Agent, or Firm* — Fish & Richardson P.C.

(57) ABSTRACT

The use of a dopamine agonist in the manufacture of a medicament for the treatment or prevention of endometriosis.

11 Claims, 7 Drawing Sheets

(56) References Cited

OTHER PUBLICATIONS

The abstract of Kletzky et al., Fert Steril, 1989;51(2):269-72.*
Chernov, Yu. No. et al., "Method for enhancing effectiveness of infertility treatment caused by small-scale external genital endometriosis", XP002443562; retrieved from STN Database accession No. 2006:332641; See parlodel (bromocriptine mesylate); abstract.
Tsakok F H et al.; "The use of bromocriptine in hyperprolactinennia and galactorrhea in Singapore", International Journal of Gynaecology and Obstetrics: the official organ of the International Federation of Gynaecology and Obsterics (Apr. 1985); vol. 23, No. 2; pp. 109-113, XP002443515; ISSN: 0020-7292; abstract; see p. 109: "abstract" and "keywords"; see p. 112 col. 1, par 2: endometriosis.
Carpenter et al., "A systematic review to determine the effectiveness of medical therapies at causing disease regression in endometriosis"; Review in Gynaecological and Perinatal Practice, Elsevier, Kidlington, GV, vol. 6, No. 3-4, (Sep. 2006); pp. 161-167; XP005625236; ISSN: 1871-2320.
Schmidt C L; "Endometriosis: a reappraisal of pathogenesis and treatment"; Fertility and Sterility; (Aug. 1985); vol. 44, No. 2; pp. 157-173; XP009086932; ISSN: 0015-0282.
Beers et al., "The Merck Index", XP002497582, 1999, pp. 1958-1959.
Novella-Maestre et al., "Antiangiogenic Action of Dopamine Agonists in Experimentally-Induced Endometriotic Lesions", Human Reproduction, 2007, 22(1), Suppl. 1: 1-47.
Gomez et al., "Effects of hyperprolactinemia treatment with the dopamine agonist quinagolide on endometriotic lesions in patients with endometriosis-associated hyperprolactinemia", Fertility and Sterility, 2011, vol. 95, No. 3, pp. 882-888.
Novella-Maestre et al., "Dopamine agonist administration causes a reduction in endometrial implants through modulation of angiogenesis in experimentally induced endometriosis", Human Reproduction, 2009, vol. 24, No. 5, pp. 1025-1035.
Non-final Rejection mailed Aug. 2, 2012 in U.S. Appl. No. 13/380,098.
Response to non-final rejection of Aug. 2, 2012 filed in USPTO on Feb. 1, 2013 in U.S. Appl. No. 13/380,098.
Final Rejection mailed Feb. 8, 2013 in U.S. Appl. No. 13/380,098.

* cited by examiner

Fig 1
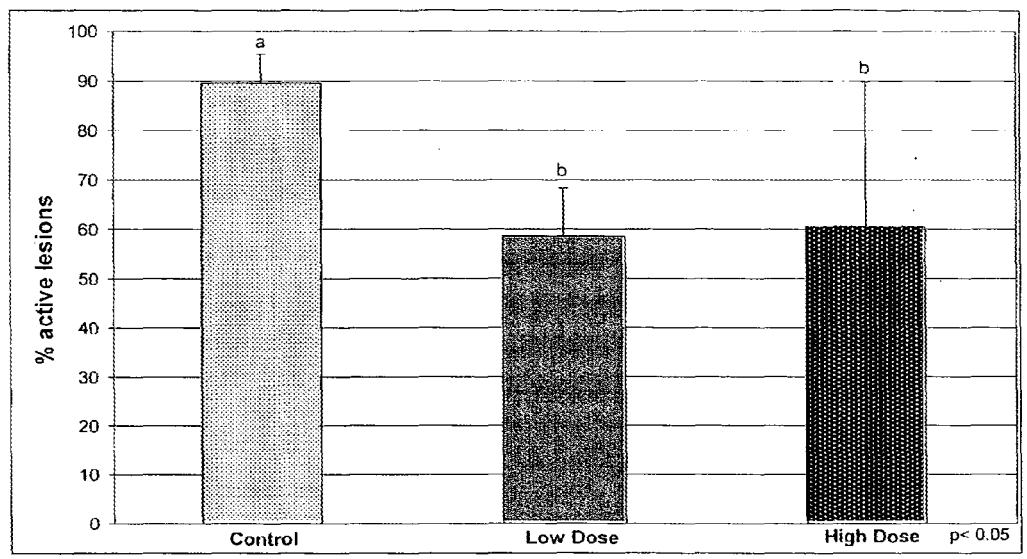
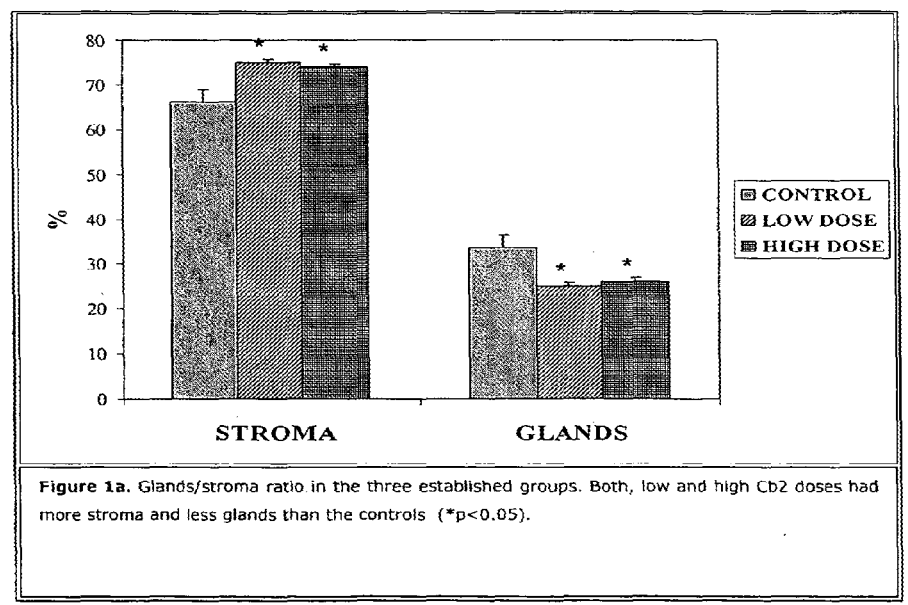
Figure 1a. Glands/stroma ratio in the three established groups. Both, low and high Cb2 doses had more stroma and less glands than the controls (*p<0.05).

Fig 2 (Angiogenic Study)

Fig 3 (Percentage)

Fig 4: Proliferation Study

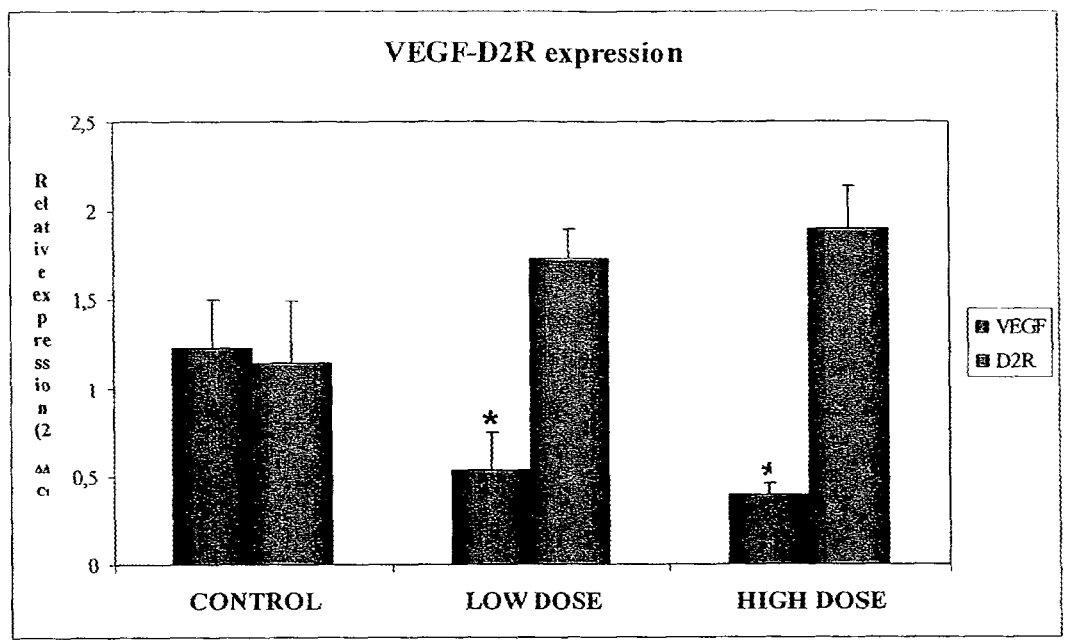
FIGURE 6a shows the expression profile of dopamine receptor 2 (Dp-r2, "D2R") and VEGF in endometrial implants of the animals in the three established groups (control, low and high dose groups)

Fig 6b
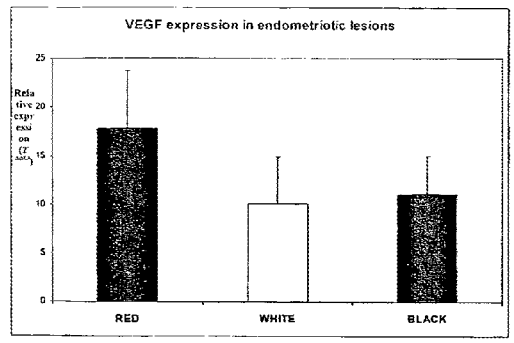
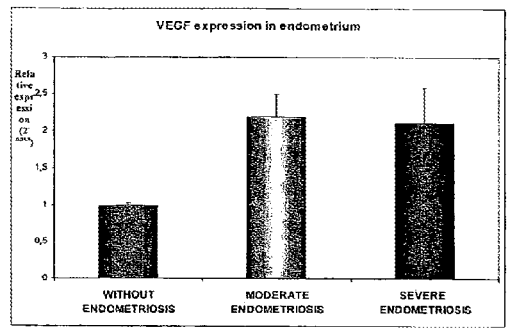
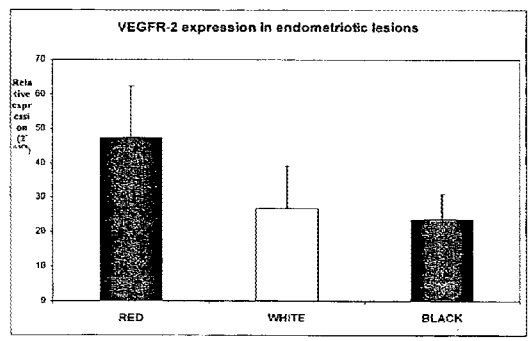
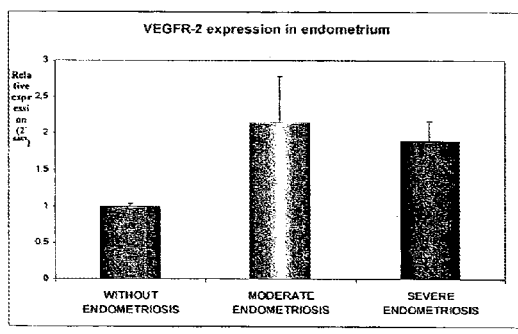
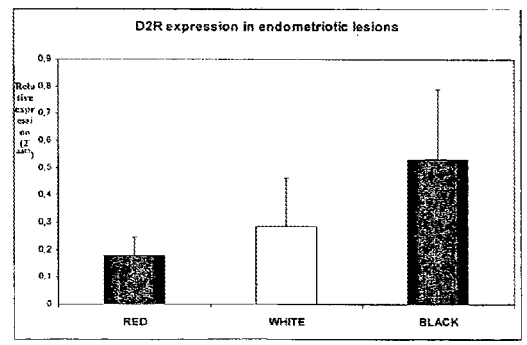
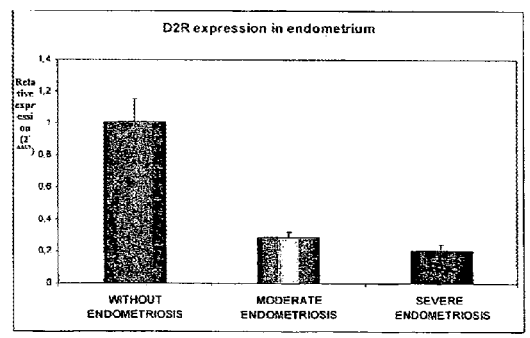

MEDICAMENT FOR THE TREATMENT OF ENDOMETRIOSIS

CROSS REFERENCE TO RELATED APPLICATIONS

The present application is a continuation of U.S. Application No. 12/525,342, filed on Dec. 29, 2009, which is the U.S. National Phase Application under 35 U.S.C. §371 of International Patent Application Serial No. PCT/IB2008/001273, filed on Feb. 1, 2008, which claims the benefit of U.S. Provisional Patent Application Ser. No. 60/947,165, filed on Jun. 29, 2007, British Patent Application Serial No. 0712626.1, filed on Jun. 29, 2007, and European Patent Application Serial No. 07250429.3, filed on Feb. 1, 2007, all of which are hereby incorporated by reference in their entireties.

The present invention relates to medicaments for the treatment of endometriosis.

Endometriosis is a benign, chronic, gynaecological disease. It may be defined as a presence of endometrial tissue, comprising both glandular epithelium and stroma, outside the uterine cavity. It is a benign gynaecological disorder, which, in a sub-population of female patients, may develop into an aggressive disease. Endometriosis is associated with various distressing symptoms including dysmenorrhoea, dyspareunia, pelvic pain and reduced fertility.

It is known that angiogenesis (the process whereby new blood vessels are formed from pre-existing vessels) may be of importance in the development of endometriosis, and that vascular permeability factor/vascular endothelial growth factor (VP/VEGF) has a role in vascular genesis, and in both physiological and pathological angiogenesis. The potential effectiveness of anti-angiogenic therapy for treating endometriosis has been assessed using a study using human endometrial tissues transplanted to immuno-compromised nude mice. Four different anti-angiogenic agents were administered three weeks after the endometrial explants had been transplanted (Nap et al, 2004). All four inhibitors were able to reduce the size of established explants, and new blood vessel formation was stopped. However, the known anti-angiogenic agents are highly toxic, and rather difficult to introduce in a human clinical setting.

It has now been unexpectedly found that compositions which include a dopamine agonist may be used to treat endometriosis.

The present invention therefore provides the use of a dopamine agonist in the manufacture of a medicament for the treatment and/or prevention of endometriosis. The present invention also provides the use of a dopamine agonist in the treatment and/or prevention of endometriosis. Herein, the term "treatment of endometriosis" includes treatment to reduce (or remove) the amount of endometrial tissue which is present outside the uterine cavity (e.g. reduction or removal of endometriotic lesions) and/or treatment to reduce and/or ameliorate one or more symptoms associated with endometriosis (e.g. treatment to ameliorate and/or reduce the symptoms of dysmenorrhoea; treatment to ameliorate and/or reduce the symptoms of dyspareunia, and/or treatment to ameliorate and/or reduce pelvic pain). The term "treatment of endometriosis" includes treatment to reduce the number of instances, and/or reduce the size of instances, of endometrial tissue which is present outside the uterine cavity (e.g. reduction of number and/or size of endometriotic lesions). The term "treatment of endometriosis" includes treatment to reduce the number of endometrial glands. The term "treatment of endometriosis" includes treatment which results in one or more of: a significant decrease in the percentage of active endometriotic lesions; a significant loss of the cellularity and organisation manifesting characteristics of atrophic or degenerative tissue in endometriotic lesions; and a significant decrease in the number of new blood vessels in endometriotic lesions. The term "treatment of endometriosis" includes treatment to reduce the number and/or size of endometriotic lesions on one or more of the ovary, the uterine cul-de-sac, the uterosacral ligaments, the posterior surfaces of the uterus, the broad ligament, the remaining pelvic peritoneum, the bowel, the urinary tract (including e.g. the bladder, and/or the ureters).

The term endometriosis includes, for example, peritoneal endometriosis, ovarian endometriosis and deep endometriosis.

Herein, the term dopamine agonist means a compound that acts like dopamine, for example, a drug which interacts (e.g. binds specifically) with a dopamine receptor to mimic a dopamine action. It does not include compounds which are exclusively "dopaminergic substances", i.e. exclusively compounds which, through different mechanisms of action, increase the levels of dopamine. The term dopamine agonist does not include the bridged indenopyrrolocarbazoles disclosed in U.S. Pat. No. 6,359,130.

Dopamine agonists have previously been found to be useful in the treatment or prevention of ovarian hyperstimulation syndrome (OHSS) (WO 2006117608). This is a condition where the capillaries increase their vascular permeability significantly. Dopamine agonists were found to be able to reverse this effect. However, the condition of endometriosis and the potential effectiveness of anti-angiogenic therapy for treating endometriosis is not disclosed here.

Dopamine agonists within the terms of the invention include, but are not limited to, amantadine, bromocryptine, cabergoline, quinagolide, lisuride, pergolide, ropinirole and pramipexole. A preferred dopamine agonist for use in the present invention is cabergoline. A preferred dopamine agonist for use in the present invention is quinagolide. The so-called "partial dopamine agonists" (e.g. terguride) may also be used in accordance with the invention. However, the use of dopamine agonists is preferred.

Preferably, a single dopamine agonist is used.

The dopamine agonist may be administered at a dose (e.g. an oral dose to a human patient) of between 25 micrograms per day and 80 mg/day, preferably between 50 micrograms per day and 5 mg/day, more preferably between 300 micrograms per day and 1 mg/day; suitable doses within this range depend to the dopamine agonist to be used, as is readily apparent to those skilled in the art.

In a preferred embodiment, the dopamine agonist is cabergoline. Preferably the cabergoline is administered at a dose (e.g. an oral dose to a human patient) of between 0.01 and 12.5 mg/week, preferably between 0.1 and 10 mg/week, more preferably between 0.5 mg and 5 mg/week, more preferably at a dose of between 3.5 mg/week and 4 mg/week. The dopamine agonist may be administered as, for example, a single daily dose (of for example, between 0.1 mg/day and 5 mg/day, from 0.2 mg/day to 1 mg/day, for example 0.5 mg/day); or the daily dose may be divided into two or more sub-doses to be taken at different times over a 24 hour period. The dopamine agonist (cabergoline) may be administered as a daily dose at the levels above, or as equivalent doses e.g. per week, twice a week, or every two days. In one regime, the dopamine agonist (for example, cabergoline) is administered at a total dose of between 3.5 and 12.5 mg per week (e.g. 4 mg per week, 7 mg per week, 10 mg/week).

In another embodiment, the dopamine agonist is quinagolide. Preferably the quinagolide is administered at a dose (e.g. an oral dose to a human patient) of between 25 and 1000 micrograms/day, preferably between 25 and 500 micrograms/day, more preferably between 25 and 300 micrograms/day. The dopamine agonist may be administered as, for example, a single daily dose; or the daily dose may be divided into two or more sub-doses to be taken at different times over a 24 hour period. The dopamine agonist (quinagolide) may be administered as a daily dose at the levels above, or as equivalent doses e.g. per week, twice a week, or every two days.

In another embodiment, the dopamine agonist is bromocryptine. Preferably the bromocryptine is administered at a dose (e.g. an oral dose to a human patient) of between 10 to 80 micrograms/day, preferably 10 to 40 mg/day.

In one embodiment, the dopamine agonist is used as the only medical treatment for endometriosis. In other words, the dopamine agonist may be used in the absence of other medical or surgical treatments [for example, in the absence of danazol].

In a further embodiment, administration of a dopamine agonist may be combined with other medical or surgical treatments for endometriosis [for example, NSAIDs and/or hormonal treatments (danazol, OCs, medroxyprogesterone acetate, other progestins, GnRH agonists and antagonists, aromatase inhibitors)]. In a further embodiment, surgical treatment or medical treatment may be used prior, during or after treatment with dopamine agonist. These embodiments are discussed in a little more detail in the examples, below.

It has also been found that administration of dopamine agonist to a patient in need thereof may provide substantial clinical benefits such as, for example: significant decrease in the percentage of active endometriotic lesions; significant loss of the cellularity and organisation manifesting characteristics of atrophic or degenerative tissue in endometriotic lesions; and significant decrease in the number of new blood vessels in endometriotic lesions.

Medicaments based on dopamine agonists have also the advantage of high dose tolerance, with safe and well documented clinical use records.

Further, it has been found that the dopamine agonist (for example, cabergoline) may be administered for long periods of time (e.g. 1 to 3 weeks (e.g. 1 to 21 days, for example 1 to 14 days), from 1 day to 3 months, 1 day to six months, 1 day to 12 months, or 1 day to 2 years, or longer) with therapeutically beneficial effect, and low risk of side effects. The administration may be continuous at e.g. daily or weekly dose, or may be interrupted by one or more interruptions of, for example, a number (e.g. 1 to 3) of weeks or a number (e.g. 1 to 3) of months. The dopamine agonist may be administered for as long as pain (or other symptom) continues.

The dopamine agonist (for example, cabergoline, quinagolide) may be administered to a pregnant subject.

The treatment or prevention of endometriosis may be associated with a decrease in the amount of endometrial glands.

In an example of the invention, vascular endothelial growth factor (VEGF) may be targeted by the dopamine agonist, as a factor in the development of endometriosis. The isoforms $VEGF_{121}$ and $VEGF_{165}$ appear to be mainly involved in the process of angiogenesis (Watkins, R. H., et al., Am. J. Physiol. 1999, vol. 276, pp. 858-67). Two specific endothelial cell membrane receptors for VEGF have been identified, VEGF receptor-1 (VEGFR-1; Flt-1) and VEGFR-2 (Flk-1/KDR). The VEGFR-2 appears to be mainly involved in regulating angiogenesis and vasculogenesis.

VEGFR-2 (KDR) may thus be targeted by the dopamine agonist, as a factor in the development of endometriosis. Notch-4 may be targeted by the dopamine agonist, as a factor in the development of endometriosis. VEGF, VEGFR-2 and Notch-4 may be targeted by the dopamine agonist, as a factor in the development of endometriosis. Other mechanisms of action of the dopamine agonist are within the scope of the invention.

The dopamine agonist is administered as a pharmaceutically acceptable preparation. Preparations may be administered in accordance with the invention in pharmaceutically acceptable compositions that may optionally comprise pharmaceutically acceptable salts, buffering agents, preservatives and excipients. Pharmaceutical preparations which include dopamine agonist(s) as active agents are well known in the art and are commercially available. For example, cabergoline is available under the registered trade marks Cabaser and Sogilen/Dostinex. The use of such commercially available dopamine agonist preparations in the treatment of endometriosis is according to the invention.

The mode of administration selected will depend on the acuteness and severity of the condition being treated, and the dosage required. Any mode of administration that produces desired therapeutic effect without unacceptable adverse effects is relevant in practicing the invention. Such modes of administration may include oral, rectal, topical, transdermal, sublingual, intramuscular, parenteral, intravenous, intracavity, vaginal, and adhesive matrix to be used during surgery. Various approaches for formulating compositions for use in accordance with the invention are described in the Handbook of Pharmaceutical Excipients, Third Edition, American Pharmaceutical Association, USA and Pharmaceutical Press UK (2000), and Pharmaceutics—The Science of Dosage Form Design, Churchill Livingston (1988).

In a preferred embodiment, the administration is oral. Compositions suitable for oral administration include capsules, cachets, tablets, syrups, elixirs or lozenges.

According to the present invention in a further aspect, there is provided a method of treatment or prevention of endometriosis comprising a step of administration to a patient in need thereof of a dopamine agonist.

Preferably the dopamine agonist is administered in the form of a pharmaceutical preparation which includes one or more dopamine agonists as the active ingredient.

The dopamine agonist may be administered at a dose (e.g. an oral dose to a human patient) of between 25 micrograms per day and 80 mg/day, preferably between 50 micrograms per day and 5 mg/day, more preferably between 300 micrograms per day and 1 mg/day; suitable doses within this range depend to the dopamine agonist to be used, as is readily apparent to those skilled in the art.

In a preferred embodiment, the dopamine agonist is cabergoline. Preferably the cabergoline is administered at a dose (e.g. an oral dose to a human patient) of between 0.01 and 12.5 mg/week, preferably between 0.1 and 10 mg/week, more preferably between 0.5 mg and 5 mg/week, more preferably at a dose of between 3.5 mg/week and 4 mg/week. The dopamine agonist may be administered as, for example, a single daily dose (of for example, between 0.1 mg/day and 5 mg/day, from 0.2 mg/day to 1 mg/day, for example 0.5 mg/day); or the daily dose may be divided into two or more sub-doses to be taken at different times over a 24 hour period. The dopamine agonist (cabergoline) may be administered as a daily dose at the levels above, or as equivalent doses e.g. per week, twice a week, or every two days. In one regime, the dopamine agonist (for example, cabergoline) is administered at a total dose of between 3.5 and 12.5 mg per week (e.g. 4 mg per week, 7 mg per week, 10 mg/week).

In another embodiment, the dopamine agonist is quinagolide. Preferably the quinagolide is administered at a dose (e.g. an oral dose to a human patient) of between 25 and 1000 micrograms/day, preferably between 25 and 500 micrograms/day, more preferably between 25 and 300 micrograms/day. The dopamine agonist may be administered as, for example, a single daily dose; or the daily dose may be divided into two or more sub-doses to be taken at different times over a 24 hour period. The dopamine agonist (quinagolide) may be administered as a daily dose at the levels above, or as equivalent doses e.g. per week, twice a week, or every two days.

In another embodiment, the dopamine agonist is bromocryptine. Preferably the bromocryptine is administered at a dose (e.g. an oral dose to a human patient) of between 10 to 80 mg/day, preferably 10 to 40 mg/day.

The administration of a dopamine agonist may be combined with other medical or surgical treatments for endometriosis [for example, NSAIDs and/or hormonal treatments (danazol, OCs, medroxyprogesterone acetate, other progestins, GnRH agonists and antagonists, aromatase inhibitors)]. In a further embodiment, surgical treatment or medical treatment may be used prior, during or after treatment with dopamine agonist.

The applicants have found that the dopamine agonist (for example, cabergoline) may be administered for long periods of time (e.g. 1 to 3 weeks (e.g. 1 to 21 days, for example 1 to 14 days), from 1 day to 3 months, 1 day to six months, 1 day to 12 months, or 1 day to 2 years, or longer) with therapeutically beneficial effect, and low risk of side effects. The administration may be continuous at e.g. daily or weekly dose, or may be interrupted by one or more interruptions of, for example, a number (e.g. 1 to 3) of weeks or a number (e.g. 1 to 3) of months. The dopamine agonist may be administered for as tong as pain (or other symptom) continues.

The patient may be pregnant.

The treatment or prevention of endometriosis may be associated with a decrease in the amount of endometrial glands.

The present invention will now be illustrated with reference to the Examples and attached drawings, in which:

FIG. 1 shows the percentage of active lesions following the animal study discussed below, for the control group, and the groups treated with low dose (0.05 mg/kg/day) and high dose (0.1 mg/kg/day) of cabergoline; FIG. 1a shows the glands/stroma ratio in the three established groups [both low and high cabergoline ("Cb2") doses had more stroma and less glands than the controls (*p<0.05)].

FIG. 6a shows the presence of dopamine receptor 2 (Dp-r2) and VEGF in endometrial implants of the animals in the three established groups (control, low and high dose groups); and FIG. 6b shows the relative expression of VEGF, VEGFR-2 (KDR) and D2R in endometriotic lesions (left-hand column) and in the endometrium (right-hand column).

Example 1

Figure 2:
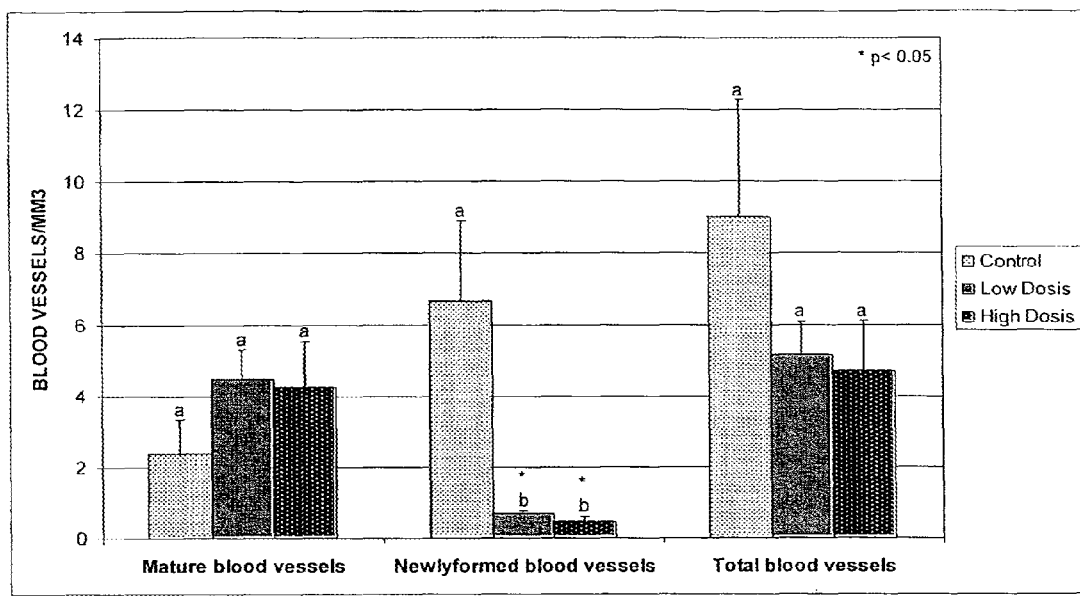
FIG. 2 shows the blood vessels (mm$^3$) for the control and low and high dose groups.

An experimental animal endometriosis model was developed in nude mice by inserting human endometrium fragments. Female mice (Hsd: Athimic Nude-nu, Harlan Ibérica S. L, Barcelona, Spain) were individually housed in autoclaved cages and bedding, in laminar flow filtered hoods. The animal room was maintained at 26 C with a 12-h light, 12-h dark cycle, and mice were fed ad libitum with autoclaved laboratory rodent chow and acidified water. All handling was performed in laminar flow filtered hoods. A mixture of ketamine/medetomidine (75 μg/g ketamine and 1 μg/g medetomidine) (Ketolar®, Parke-Davis, España; Domtor®, Pfizer, Spain) i.p injected, was used to anesthetize mice before invasive procedures and atipamezole (Antisedan®, SmithKline Beecham, Spain) 1 μg/g i.p injected, to reverse the anesthesia effects, was used after invasive procedures, using sterile instruments.

At the age of 5 weeks, sterile 60-d release capsules containing 18 mg 17β-estradiol (Innovative Research of America, Sarasota, Fla.) were placed sc in the neck of each animal. According to the manufacturer's information, capsules provide continuous release of hormone at serum concentrations of 150-250 pmol/liter, in the range of physiological levels in mice during the estrous cycle. This stable physiological level of estrogen promotes the growth of transplanted human endometrium and avoids intermouse differences related to various stages of the estrous cycle.

Four days after insertion of the estrogen pellet, an entrance was made to the peritoneal cavity in the midline in the lower abdomen to insert fresh human endometrium from ovum pick-up donors. These fragments were stuck by glue (Vetabond®, 3M Animal Care products, USA) to the peritoneum. This protocol allowed to mimic the pathologic situation of retrograde menstruation that occur in women with endometriosis.

Three weeks after implantation the animals were split into three groups. The first was a control group; the second was the low dose group, treated with 0.05 mg/kg/day oral cabergoline; and a high dose group, treated with an oral dose of 0.1 mg/kg/day cabergoline. Two weeks after treatment the animals were sacrificed and the endometriotic lesions sampled and analysed as set out below. The results are shown in FIGS. 1, 1a and 2 to 6b.

The anti-angiogenic effects of the dopamine agonists were assessed by by immunofluorescence, the antibodies used in confocal microscopy raised against Von Willebrand factor (vWF monoclonal IgG1, DAKO Corp., Denmark) present in endothelial cells and vascular smooth muscle cells (monoclonal IgG2 α-SMA-FITC conjugated de Sigma, St Louis, USA). Blood vessel which are not of new formation, are rounded by a smooth muscle layer which confers maturity to them. Identification of endothelial cells was made employing vWF, whereas mature vessels were identified by α-SMA positive staining. Thus, vWF+/αSMA− blood vessels were considered new or immature, while vWF+/αSMA+ vessels were classified as old or mature blood vessels.

Morphometric study was performed to measure the implants area and cellular density. Immunocytochemistry with Ki-67 (monoclonal IgG1 DAKO Corp., Denmark) antibody was performed in order to evaluate the proliferative activity of the implants. The histopathological and subcellular ultrastructural changes were detected using an optical microscope (OM), transmission electronic microscope (TEM) and histochemical staining. Optical microscopy (OM), transmission electron microscopy (TEM) and morphometry were performed to ascertain the presence of endometrial glands and stroma and study subcellular ultrastructural changes, area of the implants and cellular density.

TaqMan Real-time PCR and $2^{-\Delta\Delta Ct}$ methods were used to analyze the gene expression profiles of three different markers that promote angiogenesis (VEGF, VEGFR-2, Notch-4); Angiopoietin-1 (Ang-1), an antiangiogenesis marker which promotes the enlargement of existing vessels and resistance to leakage; and Wnt-1. Demonstration of the presence of the VEGF and dopamine type 2 receptor (Dp-r2) expression in experimental implants, human peritoneal endometriotic lesions, and endometrium, was conducted using the TaqMan Real-time PCR and $2^{-\Delta\Delta Ct}$ method (FIG. 6a, 6b). Similarly, this method was used to demonstrate the presence of VEGFR-2 expression in human peritoneal endometriotic lesions, and endometrium (FIG. 6b).

Statistical analysis was performed using GraphPad Instat V3.0 (GraphPad Software, San Diego, Calif., USA). The study was designed to detect differences in the different markers analyzed among treatment and control groups. Categorical data were expressed as number and percentage, and numerical data as mean ± standard error of the mean (SEM) except when specified. Significance was defined as P<0.05. One-way analysis of the variance was used for statistical analysis.

Toxicity

No mice in the study died following the administration of cabergoline. Cabergoline did not appear to change the overall health of the mice, because the body of weight of the mice in the different treatment groups was not significantly different (results not shown).

Results

FIG. 1 shows the percentage of active lesions following the animal study discussed above, for the control group, and the groups treated with low dose (0.05 mg/kg/day) and high dose (0.1 mg/kg/day) of cabergoline. Animals treated with low (58.6±9.7%) and high (60.4±8.4%) doses, had a significant decrease (p=0.0169) in active lesions as compared to controls (89.6±5.7%). The animals treated with cabergoline (both low and high dose groups) have significantly fewer active lesions when compared to the control group. In other words, treatment with cabergoline appears to reduce the number of active endometriotic lesions in this model. The OM and TEM studies showed that in the control group the endometriotic lesions presented a high cellular stroma and a histological aspect of complete reorganization and structure, as may be seen in a typical human endometriosis lesion. However, in treated lesions (high and low dose of cabergoline) a lax stroma, with lost cellularity and organization, is observed; this is characteristic of atrophic or degenerative tissue. The human endometrial stroma surrounding glandular areas, was easily differentiated from the muscular-conjunctive murine tissue.

These histological results were confirmed by morphometric analysis (FIG. 1a). Although there was no statistical difference among groups in cellular density, there was a significant (p=0.0093) difference among groups in the ratio glands/stroma, as seen in FIG. 1a; both low and high cabergoline doses had more stroma and less glands than the controls (*p<0.05). This indicates that cabergoline treatment may be associated with a decrease or reduction in the amount of endometrial glands.

FIG. 2 shows the blood vessels (mm³) for the control, low and high dosage groups, divided between "mature" blood vessels and "newly formed" blood vessels. The control group has a greater proportion of newly formed blood vessels (indicative of significant angiogenesis), while the low and high dose groups have a significantly greater proportion of mature blood vessels, suggestive of significantly reduced angiogenesis. This was also demonstrated by histology (results not shown). These results indicate that the cabergoline significantly reduced new blood vessel formation (angiogenisis), in this model.

Figure 3:
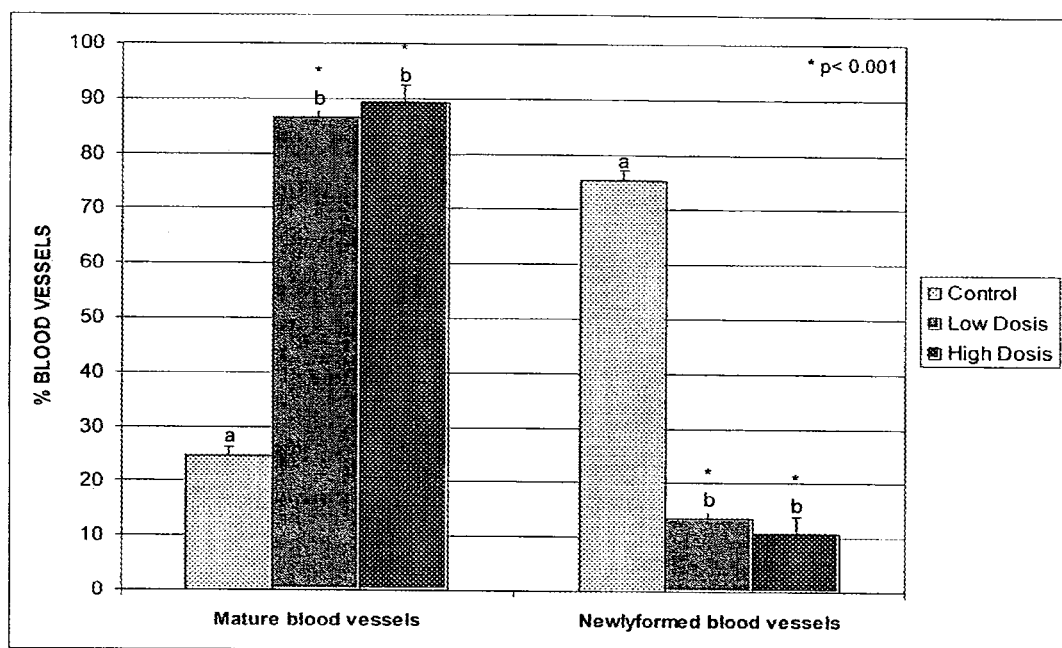
FIG. 3 shows the percentage of "mature" and "newly formed" blood vessels in the animals of the control, low and high dose groups.

FIG. 3 shows the percentage of blood vessels in the control and low and high dosage groups. The control group has approximately 74% of the total blood vessels as newly formed blood vessels, indicating significant angiogenisis. The low and high dosage groups, on the other hand, have approximately 85 to 89% of the total as mature blood vessels, indicating that angiogenisis is not significant. These results indicate that the cabergoline significantly reduced new blood vessel formation (angiogenisis), in this model.

Figure 4:
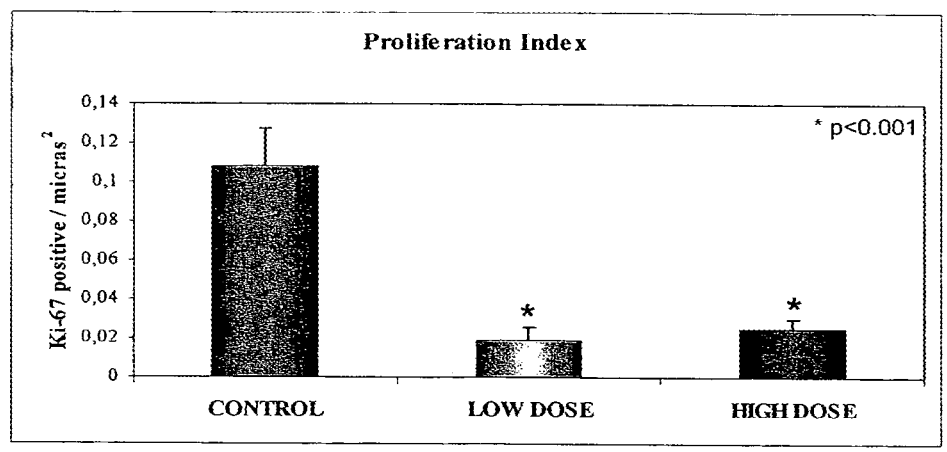
FIG. 4 shows the Proliferation Index for the control and low and high dose groups.
Figure 5:
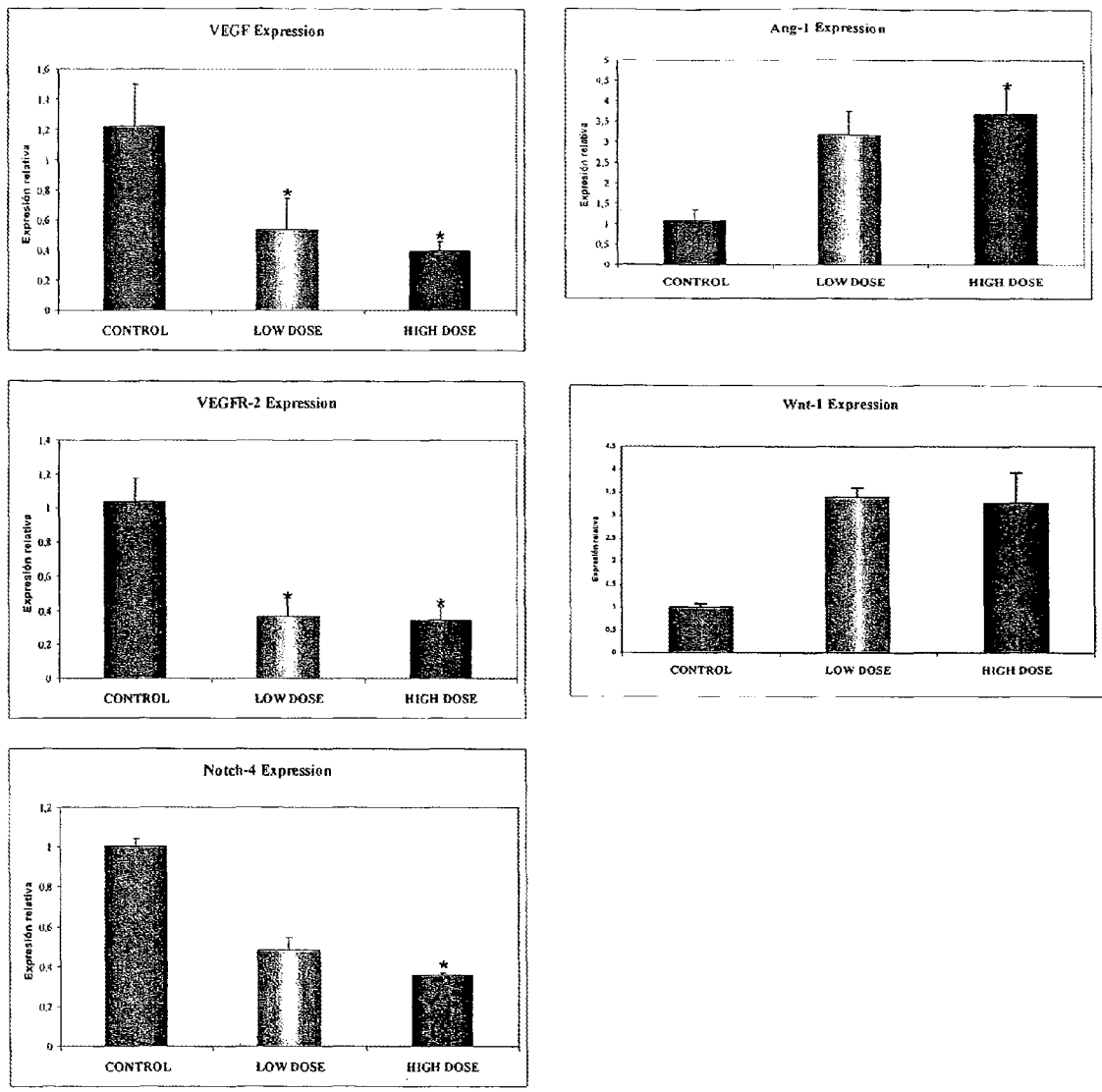
FIG. 5 shows the relative expression of VEGF, VEGFR-2 (KDR), Notch-4, Ang 1 and Wnt-1 for the control, low and high dose groups.

FIG. 4 shows the results of a proliferation study. An immunocyto chemistry study using the Ki-67 antibody (i.e. analysing the degree of cellular proliferation employing antibodies against Ki-67) was used to evaluate the proliferative activity of the implants using methods known in the art. Image counting software was used to count the Ki-67 positive cells and hence calculate the proliferation index in each group. A significant (P<0.001) decrease in proliferation was observed in lesions in animals treated with cabergoline (both low and high dose groups) compared with the control group.

The angiogenic status of the lesions was initially analyzed using immunofluorescence employing antibodies to identify new (vWF+/αSMA−) and old vessels (vWF+/αSMA+) and confocal microscopy (Leica Confocal Software). Immunofluorescence employing antibodies raised against the Von Willebrand factor (vWF) present in endothelial cells and vascular smooth muscle cells (α-SMA) can be used to test the antiangiogenic action Cb2. Blood vessel which are not of new formation, are rounded by a smooth muscle layer which confers maturity to them. Identification of endothelial cells was made employing vWF, whereas mature vessels were identified by α-SMA positive staining. Thus, vWF+/αSMA− blood vessels were considered new or immature, while vWF+/αSMA+ vessels were classified as old or mature blood vessels.

The implants presented a higher cellular stroma and the histological aspect of complete reorganization and structure typically seen in an endometriosis lesion in the control group, whereas the implants in mice included in the low and high dosage groups showed a lax stroma with loose cellularity and organization, which is characteristic of atrophic/degenerative tissue. Morphometry showed no difference in cellular density and stroma/glands glands area among groups.

TaqMan Real-time PCR and $2^{-\Delta\Delta Ct}$ methods were used to analyze the gene expression profiles of three different markers that promote angiogenesis (VEGF, VEGFR-2, Notch-4); Angiopoietin-1 (Ang-1), an antiangiogenesis marker which promotes the enlargement of existing vessels and resistance to leakage; and Wnt-1. The housekeeping 18S rRNA was used to normalize the target gene Ct values. The Ct value in each group was expressed relative to the control group Ct values (calibrator), to calculate the relative expression by the $2^{-\Delta\Delta Ct}$ method. cDNA obtained from sarcoma 180 tumor cells (S-180) and human umbilical vein endothelial cells (HUVEC) was used as negative and positive control, respectively, for the VEGF and VEGFR-2 gene expression. Spleen was used as positive control for Ang-1 and Wnt-1, and lung was employed as a Notch-4 positive control.

Table 1 shows that the gene expression profiles of pro-angiogenic markers (VEGF, VEGFR-2 and Notch-4) were downregulated in the implants treated with low and high cabergoline ("Cb2") doses compared to controls. Ang-1 and Wnt-1 are considered to be anti-angiogenic markers; their expression profiles were upregulated in the implants of mice treated with low and high Cb2 doses compared to controls, showing that cabergoline treatment is associated with angiogenesis inhibition. The relative expression data from the table are shown graphically in FIG. 5.

TABLE 1

Angiogenic gene expression profiles

| Angiogenesis marker | Gene | Control± | Vehicle | LOW DOSE (0.05 mg/kg/day) | HIGH DOSE (0.1 mg/kg/day) | p value | Expression |
|---|---|---|---|---|---|---|---|
| + | VEGF | HUVEC | 1.2 ± 0.3 | 0.5 ± 0.2 | 0.4 ± 0.1 | <0.05 | Downregulated in Cb2 treated groups |
| + | VEGFR-2 (KDR) | HUVEC | 1.0 ± 0.1 | 0.4 ± 0.1 | 0.3 ± 0.1 | <0.05 | Downregulated in Cb2 treated groups |
| + | Notch-4 | LUNG | 1.0 ± 0.1 | 0.5 ± 0.1 | 0.4 ± 0.1 | <0.05 | Downregulated in Cb2 treated groups |
| − | Ang-1 | SPLEEN | 1.1 ± 0.2 | 3.2 ± 0.6 | 3.7 ± 0.6 | <0.05 | Upregulated in Cb2 treated groups |
| − | Wnt-1 | SPLEEN | 1.0 ± 0.1 | 3.4 ± 0.2 | 3.3 ± 0.6 | =0.07 | Upregulated in Cb2 treated groups |

Data expressed as Mean ± SD

The presence of dopamine type 2 receptors in human endometrial tissue and endometriotic implants in women undergoing surgery (laparoscopy) was investigated. TaqMan Real-time PCR and $2^{-\Delta\Delta Ct}$ methods were used to to ascertain the presence of dopamine receptor 2 ("Dp-r2", "D2R") and VEGF in human endometrial tissue, not only in implants (FIG. 6a), but also in peritoneal endometriotic lesions obtained from 10 women at laparoscopy (FIG. 6b—which also includes data for VEGFR-2). Positive and negative controls for Dp-r2 were HUVEC and S-180 cDNA cells, respectively. In mice, the control Ct values were used as a calibrator, and in human peritoneal lesions the HUVEC Ct values were employed as calibrator to calculate the relative expression by $2^{-\Delta\Delta Ct}$ method.

FIG. 6a shows the presence of VEGF and Dp-r2 in endometrial implants of the animals in the three established groups. There was a trend towards increased Dp-r2 expression as the animals were treated with increasing doses of cabergoline. There is a trend towards decreased VEGF expression as the animals were treated with increasing doses of cabergoline.

FIG. 6b shows (left-hand column) the relative expression of VEGF, VEGFR-2 (KDR) and D2R ("Dp-r2") in different types of endometriotic lesions; red, white and black. There is a clear difference in VEGF, VEGFR-2 and Dp-r2 expression according to the type of lesion.

FIG. 6b also shows (right-hand column) the relative expression of VEGF, VEGFR-2 (KDR) and D2R ("Dp-r2") in the endometrium. The relative expression of VEGF and VEGFR-2 in the endometrium of subjects with endometriosis is higher than those without endometriosis; the relative expression of Dp-r2 in the endometrium of subjects with endometriosis is lower than those without.

These results are shown in Table 2, below.

The results indicate that the dopamine agonist cabergoline, administered at a dose of 0.05 and 0.1 mg/kg/day, was able to:
(a) significantly decrease the number of active endometriotic lesions;
(b) cause loss of cellularity and organisation presenting characteristics in atrophic or degenerative tissue in the endometriotic implants;
(c) significantly decrease the number of new blood vessels in the endometrioic implants;
(d) significantly decrease expression of markers of angiogenesis, and cellular proliferation; and
(e) increase tissue degeneration and reduce the endometriotic implants.

There is a high homology between the human and rodent VEGF systems which offers an indication that the activity shown in the above rodent model is applicable to human models. The results indicate that administration of dopamine agonists has a significant effect on endometriosis, possibly linked to action on angiogenesis. The results may be related to the presence of dopamine receptors in eutopic and ectopic endometrial tissue.

Example 2

A formulation as a tablet for oral use is 0.5 mg of cabergoline (commercially available as Dostinex®, Pfizer, Spain).

FURTHER EXAMPLES

Example A

A patient undergoes diagnostic laparoscopy after suffering chronic pelvic pain and is diagnosed with endometriosis type

| Gene | ENDOMETRIUM | | | | ENDOMETRIOTIC LESIONS | | | |
|---|---|---|---|---|---|---|---|---|
| | WITHOUT ENDOMETRIOSIS | MODERATE | SEVERE | P value | RED | WHITE | BLACK | P value |
| VEGF | 1.0 ± 0.1 | 2.2 ± 0.7 | 2.1 ± 0.4 | NS | 17.8 ± 5.8 | 10.1 ± 4.8 | 11.1 ± 3.9 | NS |
| KDR | 1.0 ± 0.1 | 2.1 ± 0.6 | 1.9 ± 0.3 | NS | 47.4 ± 15.0 | 26.9 ± 12.2 | 23.6 ± 7.2 | NS |
| D2R | 1.0 ± 0.1 | 0.3 ± 0.1 | 0.2 ± 0.1 | =0.07 | 0.2 ± 0.1 | 0.3 ± 0.2 | 0.6 ± 0.3 | NS |

III. At the same laparoscopy, the patient undergoes surgery such as resection of available lesions and administration of cabergoline is initiated.

Example B

Patient diagnosed previously of endometriosis, presenting with symptoms of pelvic pain and dysmenorrhea. Administration of cabergoline is initiated without surgery.

Example C

Patient diagnosed with endometriosis undergoing treatment with GnRH agonists (or danazol or aromatase inhibitors) and administration of cabergoline is initiated (with continued use of GnRH agonist) for a period. After a further 3 or 6 months of no therapy, patient restarts cabergoline for a further period.

The invention claimed is:

1. A method for the treatment of endometriosis, comprising vaginally administering a dopamine agonist to a patient in an amount sufficient to reduce or eliminate endometrial tissue outside the uterine cavity of the patient.

2. The method of claim 1, wherein the dopamine agonist is quinagolide.

3. The method of claim 2, wherein the quinagolide is administered at a dose of between 25 and 1000 micrograms/day.

4. The method of claim 2, wherein the quinagolide is administered at a dose of between 25 and 500 micrograms/day.

5. The method of claim 2, wherein the quinagolide is administered at a dose of between 25 and 300 micrograms/day.

6. The method of claim 2, wherein the quinagolide is administered for a period of between 1 day and 2 years.

7. The method of claim 2, wherein the quinagolide is administered continuously during the period.

8. The method of claim 2, wherein the quinagolide is administered in combination with other surgical or medicinal treatment for endometriosis.

9. The method of claim 2, wherein the quinagolide is administered into a pregnant patient.

10. The method of claim 2, wherein the treatment of endometriosis is associated with a decrease in the amount of endometrial glands.

11. The method of claim 2, wherein the treatment of endometriosis is associated with reduction or removal of an amount of endometrial tissue which is present outside the uterine cavity, and/or treatment to reduce and/or ameliorate one or more symptoms associated with endometriosis.

* * * * *